United States Patent [19]
Garcia et al.

[11] 3,956,259
[45] May 11, 1976

[54] FRACTIONATION OF BLOOD USING BLOCK COPOLYMER OF ETHYLENE OXIDE AND POLYOXYPROPYLENE POLYMER TO RECOVER FRACTION SUITABLE FOR ORGAN PERFUSATE

[75] Inventors: Luis A. Garcia, Huntington Beach; Guido A. Ordonez, Laguna Beach, both of Calif.

[73] Assignee: Baxter Laboratories, Inc., Deerfield, Ill.

[22] Filed: June 6, 1974

[21] Appl. No.: 476,961

Related U.S. Application Data
[62] Division of Ser. No. 327,893, Jan. 30, 1973.

[52] U.S. Cl. .......................... 260/112 B; 424/101; 424/177
[51] Int. Cl.² ......................................... C07G 7/00
[58] Field of Search ............................... 260/112 B

[56] References Cited
UNITED STATES PATENTS

| | | | |
|---|---|---|---|
| 2,390,074 | 12/1945 | Cohn | 260/122 |
| 3,415,804 | 12/1968 | Polson | 260/112 B |
| 3,450,502 | 6/1969 | Hymes | 23/258.5 |
| 3,560,475 | 2/1971 | Fekete et al. | 260/112 B |
| 3,631,018 | 12/1971 | Shanbrom et al. | 260/112 B |
| 3,682,881 | 8/1972 | Fekete et al. | 260/112 B |
| 3,763,135 | 10/1973 | Shanbrom et al. | 260/112 B |
| 3,770,631 | 11/1973 | Fekete et al. | 210/53 |
| 3,850,903 | 11/1974 | Garcia et al. | 260/112 B |

Primary Examiner—Howard E. Schain
Attorney, Agent, or Firm—Louis Altman; Lawrence W. Flynn; Max D. Hensley

[57] ABSTRACT

A method of fractionating coagulation factor-depleted blood serum or plasma by selective precipitation with block copolymers of ethylene oxide and polyoxypropylene polymer to provide immunoglobulin preparations, albumin-containing fractions and organ perfusates.

2 Claims, No Drawings

FRACTIONATION OF BLOOD USING BLOCK COPOLYMER OF ETHYLENE OXIDE AND POLYOXYPROPYLENE POLYMER TO RECOVER FRACTION SUITABLE FOR ORGAN PERFUSATE

This is a division of application Ser. No. 327,893, filed Jan. 30, 1973.

This invention relates to a method of separating proteinaceous and lipid materials from blood serum and plasma. More particularly, the invention relates to fractionation of coagulation factor-depleted blood serum and plasma.

Blood comprises a fluid containing the red and the white blood cells and the blood platelets. The plasma, or fluid part of blood, contains about 90% water and 10% solids. These solids consist essentially of about 7–9% proteins, 1% salts, and the remainder lipids and other substances. Freshly drawn blood clots within a few minutes. Formation of the clot is a complex process in which the protein, fibrinogen, is converted into insoluble fibrin. Blood serum is plasma from which this fibrin has been removed.

Fractionation of blood plasma and serum and the laboratory and clinical use of the separted blood components is common practice today. Among the various components separated from blood are albumin, $\alpha 1$-globulins, $\alpha 2$-globulins, $\beta$-globulins, $\gamma$globulins, fibrinogen, prothrombin, antihemophilic globulin, lipoproteins, thromboplastin, complement components, isoagglutinins, cholesterol, phosphatides, and numerous enzymes, e.g., amylase, fibrinolysin, esterase, and phosphatase. Various methods have been developed heretofore for separating and purifying the foregoing and other blood components. These methods generally comprise one or more of the following procedures:

a. fractional precipitation with ammonium sulfate and similar salts;

b. organic solvent precipitation with cold ethanol or acetone and other such alcohols and ketones;

c. selective adsorption on calcium phosphate gels or with barium sulfate;

d. isoelectric precipitation by pH adjustment to the point at which therre is no net charge on a given protein; and e. chromatography by use of absorbents such as CM- or DEAE-cellulose or by "Sephadex" gel filtration.

Other more recently developed procedures for selectively fractionating and purifying blood proteins involve the use of amino acids such as glycine and beta alanine, water-soluble organic polymers such as polyethylene glycol and polypropylene glycol, and water-insoluble polyelectrolyte polymers containing basis amino groups such as the dimethylaminopropylimide group.

In accordance with the present invention, a new and improved method is provided for fractionating coagulation factor-depleted blood serum and plasma. The method comprises selective precipitation with certain block copolymers which are ethylene oxide-propylene glycol condensation products. Separation of various blood components with these block copolymers has been found to be substantially and significantly better than with the polymeric polyethylene glycol. These improvements consist of increased yield and higher purity of the precipitated protein substances, greater clarity and stability of the resulting liquid serum products, and more rapid separation of the desired components.

The ethylene oxide-propylene glycol condensation products employed in this invention can be prepared by condensing ethylene oxide with polyoxypropylene polymer. A further description of the preparation of these block copolymers is found in U.S. Pat. No. 2,674,619. These block copolymers can be represented by the following structural formula:

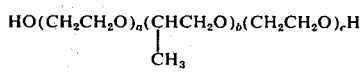

For purposes of this invention, these block copolymers desirably contain at least 50% ethylene oxide in the molecule and a polyoxypropylene hydrophobic base molecular weight of at least 950. Materials containing less than 50% ethylene oxide are not sufficiently non-toxic and products having a hydrophobic base molecular weight less than 950 do not have the desired solubility characteristics. In this respect, the block copolymers employed in this invention are related to and include materials used as blood plasma substitutes and for priming heart-lung apparatus as described in U.S. Pat. Nos. 3,450,502, 3,577,522 and 3,590,125, which are incorporated herein by reference.

Illustrative examples of suitable block copolymers are the F-38 and F-68 "PLURONIC" polyols sold by Wyandotte Chemicals Corp. F-38 contains 80% of polyoxyethylene hydrophilic units in the molecule and the polyoxypropylene hydrophobic base has a molecular weight of 950. F-68 also contains 80% of polyoxyethylene hydrophilic units in the molecule but the hydrophobic base has a molecular weight of 1750. The total molecular weight of these two "PLURONIC" polyols is 4750 and 8750, respectively. A further description of these polyols is found in the bulletin of Wyandotte Chemicals Corp. "The Pluronic Grid", Sixth Edition, which is incorporated, herein by reference.

The coagulation factor-depleted blood serum and plasma employed in this invention is blood serum and plasma from which essentially all the blood coagulation factors have been removed, especially fibrinogen (Factor 1), antihemophilic factor (Factor VIII), and the prothrombin complex factors (Factors II, VII, LX, and X). Methods for removing these factors from blood serum and plasma are known and described, for example, in U.S. Pat. Nos. 3,415,804; 3,560,475; 3,631,018; 3,652,530; and 3,682,881.

In accordance with the present invention, fractionation of coagulation factor-depleted blood serum is carried out to provide improved immunoglobulin preparations, albumin-containing fractions and organ perfusates. The immunoglobulin preparations include immunoglobulin complex ($I_gM$, $I_gA$, $\alpha_2$-macroglobulin, and plasminogen), immune serum globulin and the intravenous gamma globulin disclosed in co-pending application Ser. No. 309,841, filed Nov. 27, 1972, and assigned to a common assignee. The albumin-containing fractions include normal serum albumin, plasma protein fractions (containing 83–90% albumin and the balance $\alpha$- and $\gamma$-globulins), and plasma expanders. The organ perfusates are proteinaceous solutions suitable for the maintenance and preservation of organs for transplantation.

The selective precipitation of the present invention is carried out by the following sequency of steps:

The starting coagulation factor-depleted blood serum or plasma is diluted with water or other aqueous media to a protein concentration of from about 0.5% to about 2.5%. The diluted material is adjusted to a pH of from about 7 to about 8 and thoroughly mixed with the block copolymer to a concentration of from about 10% to about 20%. The resulting precipitate is further fractionated to provide the above-defined immunoglobulin preparations, and the supernatant is further fractionated to provide the aforementioned albumin-containing fractions. Alternatively, the diluted coagulation factor-depleted blood serum or plasma starting material can be fractionated as hereinbelow described to provide an organ perfusate.

The precipitate collected from the initial fractionation with the block copolymer at 10% – 20% concentration may contain residual amounts of prothrombin and/or albumin which are first removed. Residual prothrombin is removed by diluting the precipitate with physiologically normal saline (0.9% NaCl) to a protein concentration of from about 0.5% to about 2.5%. The diluted material is adjusted to a pH of from about 6.7 to about 7.7 and thoroughly mixed with a suitable adsorbent, such as calcium phosphate, to a concentration of from about 0.5% to about 1.5%. The resulting precipitate is separated from the supernatant and discarded. Residual albumin is then removed by adjusting the supernatant to a pH of from about 6.5 to 7.5 and thoroughly mixing with the block copolymer to a concentration of from about 9% to about 19%. The resulting precipitate is retained for further treatment to obtain the immunoglobulin preparations of the present invention and the supernatant is discarded.

The precipitate collected from the treatment for removal of residual prothrombin and albumin is diluted with normal saline to a protein concentration of from about 0.5% to about 2.5%. The diluted material is adjusted to a pH of from about 4 to about 5 and thoroughly mixed with the block copolymer to a concentration of from about 3% to about 13%. The resulting precipitate is collected and retained as the desired immunoglobulin complex and the supernatant is retained for further treatment to provide immune serum globulin and intravenous gamma globulin products.

The supernatant from the immunoglobulin complex separation is adjusted to a pH from about 4.5 to about 5.5 and thoroughly mixed with the block copolymer to a concentration of from about 4% to about 14%. The resulting precipitate is discarded. The supernatant is adjusted to a pH of from about 6.5 to about 7.5 and thoroughly mixed with the block copolymer to a concentration of from about 10% to about 20%. The resulting precipitate is collected and retained as a fraction containing greater than 90% gamma globulin. It can be resuspended in buffered aqueous solution to a protein concentration of 15.5% – 17.5% as an immune serum globulin for intramuscular use or at a protein concentration of 5% – 7% for intravenous use.

The albumin-containing supernatant collected from the initial fractionation with the block copolymer at 10% – 20% concentration, maintained at a pH of from about 7 to about 8, is thoroughly mixed with the the block copolymer to a concentration of from about 17% to about 27%. The resulting precipitate is discarded. The supernatant is adjusted to a temperature of from about 0° C. to about 10° C., to a pH of from about 4 to about 5, and thoroughly mixed in acetate buffer (4 molar acetic acid, 0.8 molar sodium acetate, pH 4.0). The resulting precipitate is collected and retained for further treatment to provide serum albumin and plasma protein fractions and the supernatant is discarded.

A purified serum albumin solution for therapeutic use can be made by first heat treating the collected precipitate to remove alpha and beta globulins as described, for example, in U.S. Pat. No. 2,765,299. The precipitate is dissolved in normal saline to a protein concentration of from about 4% to about 8%. Sodium caprylate is added to a concentration of from about 0.0075 to about 0.02 molarity and the pH is adjusted to from about 5 to about 5.2. This suspension is heated from about one to about four hours at a temperature of from about 65° to about 75° C. with constant stirring. The denatured proteins are then removed by centrifugation and/or filtration and the protein concentration is adjusted to from about 0.5% to about 2.5% by mixing with normal saline.

Following this heat treatment, the block copolymer is added to a concentration of from about 15% to about 35%, the suspension is cooled to a temperature of from about 0° to about 10° C., the pH is adjusted to from about 4 to about 5 with acetate buffer (as described hereinbefore), and the suspension thoroughly mixed. The resulting precipitate is retained and the supernatant is discarded. A 5% or 25% normal serum albumin solution is prepared by resuspending the precipitate in normal saline to the appropriate protein concentration. The ionic concentration is adjusted to 154 meq./l. Na$^-$, 124 meq./l. Cl$^-$, and 0.04 meq./l. K$^+$, or other suitable ionic levels.

Alternatively, a plasma protein fraction can be made by resuspending the collected precipitate in aqueous media to a protein concentration of from about 6% to about 7%. The suspension is heated for 2 hours at 55°–65° C. and then clarified by centrifugation and/or filtration. The ionic concentration is adjusted to 100–120 meq./l. Na$^+$, 45–55 meq./l. Cl$^-$, and not in excess of 2 meq./l. K$^+$, and the protein content adjusted to 5–5.6 gm. %. This material can be used as a primary plasma volume expander.

An organ perfusate is prepared from the hereinbefore diluted coagulation factor-depleted blood serum or plasma starting material as follows.

The diluted material may contain residual amounts of prothrombin. Residual prothrombin is removed by first adjusting the pH to a level of from about 5.5 to about 6.5. Fibrinogen is then thoroughly mixed with the suspension to a concentration of from about 0.1% to about 1.5%. The pH is adjusted to a level of from about 6.7 to about 7.7 and the suspension is then thoroughly mixed with a suitable adsorbent, such as calcium phosphate, to a concentration of from about 0.5% to about 1.5%. The resulting precipitate is separated from the supernatant and discarded.

The retained supernatant is adjusted to a pH of from about 4 to about 5 and the block copolymer thoroughly admixed therewith to a concentration of from about 2% to about 12%. The resulting precipitate, which is rich in lipoproteins, is separated from the supernatant and discarded. Additional proteinaceous material is removed from the remaining supernatant by thoroughly mixing with the block copolymer to a concentration of from about 14% to about 24%, cooling the suspension to a temperature of from about 0° C. to about 10° C. and adjusting the pH to a level of from about 4 to about 5 with acetate buffer (as hereinbefore described). The resulting precipitate is separated from the supernatant which is discarded. The precipitate is then resuspended in aqueous media to a protein concentration of from about 4% to about 8%, to provide the desired organ perfusate.

The following examples will further illustrate the invention although the invention is not limited to these specific examples.

EXAMPLE 1

Coagulation factors are removed from a pool of frozen normal human plasma by the following procedure. In this example the block copolymer is "PLURONIC"F-38.

a. The frozen plasma is quickly thawed and adjusted to pH 6.88. Sufficient glycine is added to bring the concentration to 2.3 molar and the mixture is mechanically stirred for 1 to 4 hours at 2° C. and then centrifuged. The precipitate is retained and processed for the production of antihemophilic factor (AHF, Factor VIII) and fibrinogen, and the supernatant is processed for removal of prothrombin complex in part (b).

b. The supernatant from part (a) is diluted to double its volume with normal saline and adjusted to pH 6. Block copolymer is added to a concentration of 35% (weight basis) and the mixture is mechanically stirred for 1 to 2 hours at room temperature (20° C.). The suspension is centrifuged and the supernatant is discarded. The precipitate is then suspended in normal saline to a protein concentration of 5% and the pH is adjusted to 7.2. Tribasic calcium phosphate $[Ca_{10}(OH)_2(PO_4)_6]$ is added to a concentration of 0.5% and the mixture is mechanically stirred for 1 hour at 20° C. and then centrifuged. The precipitate is retained and processed for the production of prothrombin complex, and the supernatant is processed for the production of immunoglobulin preparations, albumincontaining fractions and organ perfusates.

c. One part of the supernatant from part (b) is diluted with distilled water to a protein concentration of 1% and adjusted to pH 7.5. Block copolymer is added to a concentration of 15% and the mixture is mechanically stirred for one to two hours and then centrifuged. The precipitate is retained as a high molecular weight protein fraction for separation of macroglobulins and immune serum globulin. The supernatant is retained as a lower molecular weight protein fraction for separation of albumincontaining fractions.

d. The precipitate from part (c) is suspended in normal saline to a protein concentration of 1%. Tribasic calcium phosphate is then added to the suspension to a concentration of 0.5% and the pH is adjusted to 7.2. The mixture is mechanically stirred for one hour, followed by centrifugation. The precipitate is discarded and the supernatant is adjusted to pH 7, followed by addition of block copolymer to a concentration of 14%. Mechanical stirring is carried out for 1 to 2 hours at 20° C., followed by centrifugation. The supernatant, containing traces of albumin, is discarded and the precipitate is suspended in normal saline to a protein concentration of 1%. The suspension is adjusted to pH 4.5, followed by the addition of block copolymer to a concentration of 8%. The mixture is mechanically stirred for one to two hours at room temperature, followed by centrifugation. The precipitate is retained as a crude immunoglobulin complex which contains $\alpha_2$-macroglobulin, IgM, IgA, and plasminogen.

e. The supernatant from part (d) is adjusted to pH 5 and the block copolymer is added to a concentration of 9%. The mixture is mechanically stirred for one to two hours at room temperature, followed by filtration. The precipitate, which contains complement factors, is discarded. The supernatant is adjusted to pH 7 and the block copolymer added to a concentration of 16%. The mixture is mechanically stirred for 1 to 2 hours, followed by centrifugation, and the resulting supernatant is discarded. The precipitate is suspended in glycine-saline solution (0.3 molar glycine/1% NaCl) to both 6% protein and 16.5% protein levels, respectively. Samples of gamma globulin prepared by this process were shown to have the characteristics of immune serum globulin made by the Cohn ethanol fractionation method, as determined by ultracentrifugation, Tiselius electrophoresis, immunoelectro-phoresis, and antibody content. However, the product made by this process desirably had a substantially lower anti-complementary titer as compared to said Cohn fractionated product.

f. The supernatant from part (c) is maintained at pH 7.5 and mixed with the block copolymer to a concentration of 22% copolymer. The mixture is mechanically stirred for one to two hours at room temperature, followed by centrifugation. The precipitate, which contains traces of IgG and alpha and beta globulins, is discarded. The supernatant is mixed with normal saline to a concentration of 0.9% NaCl, chilled to 5° C., adjusted to pH 4.5 with acetate buffer (0.8 molar sodium acetate, 4 molar acetic acid, pH 4) and stirred for 1 to 2 hours, followed by centrifugation. The supernatant is discarded and one part of the precipitate is resuspended in normal saline to a protein concentration of 5%. This can be retained as a plasma protein fraction or further processed to obtain pure albumin.

g. Another part of the precipitate in part (f) is suspended in distilled water, adjusted to pH 5.1, and heat treated at 70° C. with stirring for 1 to 4 hours in the presence of 0.012 molar sodium caprylate. The resulting precipitate is discarded. The supernatant is mixed with normal saline to a concentration of 0.9% NaCl and then mixed with the block copolymer to a concentration of 19% copolymer. After chilling the material to 5° C., the pH is adjusted to 4.5 with acetate buffer, the mixture is mechanically stirred for 1 to 2 hours and then centrifuged. The supernatant is discarded and the precipitate is suspended in saline to 5% and 25% protein concentrations, respectively. Samples of albumin solutions made by this process were shown to have the same physiochemical characteristics of the albumin made by the Cohn ethanol fractionation process, as determined by ultracentrifugation, Tiselius electrophoresis, immunoelectro-phoresis and osmolarity.

h. Another part of the supernatant from part (b) is diluted with normal saline to a protein concentration of 1% and adjusted to pH 6. Fibrinogen is then added to a concentration of 0.5 grams per Kilogram of supernatant. The mixture is mechanically stirred for 2 hours at room temperature and the mixture then is adjusted to pH 7.2. Tribasic calcium phosphate is added to a concentration of 0.5%. After mixing for 1 to 2 hours, the mixture is centrifuged and the precipitate discarded. The supernatant is adjusted to pH 4.5 and the block copolymer is added to a concentration of 7%. The mixture is stirred for one to two hours, followed by centrifugation. The resulting precipitate is discarded and the supernatant is mixed with the block copolymer to a concentration of 19%. The suspension is chilled to 5° C. and adjusted to pH 4.5 with acetate buffer. After mixing 2 hours, the mixture is centrifuged and the supernatant is discarded. The precipitate is suspended in water to a protein concentration of 6% and the electrolytes are adjusted to that of plasma. This product is useful for organ perfusion at 5°C. without the formation of particulate matter.

EXAMPLE 2

The procedure of Example 1 is repeated except that "PLURONIC" F-68 is substituted for an equivalent amount of the "PLURONIC" F-38 with substantially similar results.

Various other examples and modifications of the foregoing examples will be apparent to those skilled in the art after reading the foregoing disclosure. All such further examples and modifications as come within the spirit and scope of the invention are included in the appended claims.

What is claimed is:

1. The process of preparing a blood fraction suitable for use as an organ perfusate from coagulation factor-depleted blood serum and plasma comprising selective precipitation by admixing with from about 2% to about 12% of a compound of the formula

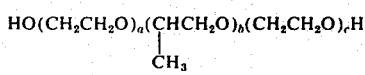

wherein $a$ and $c$ are integers such that the hydrophile portion represented by ($CH_2CH_2O$) constitutes at least about 50% of the molecule and $b$ is an integer such that the hydrophobic portion represented by

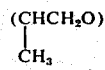

has a molecular weight of at least about 950 at a pH from about 4 to 5, separating the resulting precipitate from the supernatant and then adjusting the concentration of said copolymer in said supernatant to from about 14% to about 24% and adjusting to a pH of from about 4 to about 5 with acetate buffer at a temperature of from about 0° C to about 10° C to provide a precipitate for reconstitution to the desired organ perfusate.

2. The process of claim 1 in which the block copolymer contains about 80% of polyoxyethylene hydrophilic units in the molecule and the polyoxypropylene hydrophobic base has a molecular weight of about 950.

* * * * *